US009460701B2

(12) United States Patent
Yong et al.

(10) Patent No.: US 9,460,701 B2
(45) Date of Patent: Oct. 4, 2016

(54) SYSTEMS AND METHODS FOR ADAPTIVE NOISE CANCELLATION BY BIASING ANTI-NOISE LEVEL

(71) Applicant: Cirrus Logic, Inc., Austin, TX (US)

(72) Inventors: Chin Huang Yong, Austin, TX (US); Jeffrey D. Alderson, Austin, TX (US)

(73) Assignee: Cirrus Logic, Inc., Austin, TX (US)

( * ) Notice: Subject to any disclaimer, the term of this patent is extended or adjusted under 35 U.S.C. 154(b) by 465 days.

(21) Appl. No.: 13/943,454

(22) Filed: Jul. 16, 2013

(65) Prior Publication Data

US 2014/0314244 A1 Oct. 23, 2014

Related U.S. Application Data

(60) Provisional application No. 61/812,842, filed on Apr. 17, 2013.

(51) Int. Cl.

| | |
|---|---|
| ***A61F 11/06*** | (2006.01) |
| ***G10K 11/16*** | (2006.01) |
| ***G10K 11/178*** | (2006.01) |

(52) U.S. Cl.

CPC ............. *G10K 11/16* (2013.01); *G10K 11/178* (2013.01); *G10K 2210/1081* (2013.01); (Continued)

(58) Field of Classification Search

CPC ............ H04R 3/02; H04R 3/04; H04R 3/06; H04R 3/08; H04R 3/14; H04R 3/007; H04R 5/04; H04R 25/453; H04R 25/50; H04R 25/505; H04R 25/507; H04R 1/1091; H04R 1/10; H04R 1/08; H04R 29/001; H04R 3/00; H04R 3/002; H04R 2420/07; H04R 2499/11; H04R 2217/03; H04R 2225/41; H04R 2225/43; H03G 5/00; H03G 5/005; H03G 5/16; H03G 5/165; H03G 5/24; H03G 5/28; H03G 9/005; H03G 9/24; H03G 9/025; H03G 2201/702; H03G 7/007; G06F 3/165; G06F 17/3074; G10K 11/175; G10K 11/16

USPC ......... 381/28, 59, 55, 317, 318, 321, 74, 72, 381/26, 56, 57, 71.1, 71.11, 71.14, 83, 332, 381/93, 96, 97, 98, 99, 100, 101, 102, 103, 381/106, 107, 108, 120, 121; 327/551, 552, 327/553, 555, 560; 704/E21.007, E21.02; 379/406.1–406.16; 455/570

See application file for complete search history.

(56) References Cited

U.S. PATENT DOCUMENTS

| | | | |
|---|---|---|---|
| 5,251,263 A | 10/1993 | Andrea et al. | |
| 5,278,913 A | 1/1994 | Delfosse et al. | |

(Continued)

FOREIGN PATENT DOCUMENTS

| | | | | |
|---|---|---|---|---|
| AT | WO 2012119808 A2 * | 9/2012 | ......... | G10K 11/1784 |
| DE | 102011013343 A1 | 9/2012 | | |

(Continued)

OTHER PUBLICATIONS

Widrow, B. et al., Adaptive Noise Cancelling: Principles and Applications, Proceedings of the IEEE, IEEE, New York, NY, U.S., vol. 63, No. 13, Dec. 1975, pp. 1692-1716.

(Continued)

*Primary Examiner* — Leshui Zhang

(74) *Attorney, Agent, or Firm* — Jackson Walker L.L.P.

(57) ABSTRACT

A processing circuit may comprise an adaptive filter having a response generating an anti-noise signal from a reference microphone signal, a secondary path estimate filter modeling an electro-acoustic path of a source audio signal, a biasing portion that generates a scaled anti-noise signal by applying a scaling factor and the response of the secondary path estimate filter to the anti-noise signal, and a coefficient control block that shapes the response of the adaptive filter in conformity with the reference microphone signal and a modified playback corrected error signal by adapting the response of the adaptive filter to minimize ambient audio sounds in the error microphone signal, wherein the playback corrected error is based on a difference between the error microphone signal and the source audio signal and the modified playback corrected error signal is based on a difference between the playback corrected error signal and the scaled anti-noise signal.

27 Claims, 3 Drawing Sheets

(52) U.S. Cl.
CPC ................ *G10K 2210/3014* (2013.01); *G10K 2210/3017* (2013.01); *G10K 2210/3022* (2013.01); *G10K 2210/3027* (2013.01); *G10K 2210/30351* (2013.01)

(56) References Cited

U.S. PATENT DOCUMENTS 5,321,759 A 6/1994 Yuan
5,337,365 A 8/1994 Hamabe et al.
5,359,662 A 10/1994 Yuan et al.
5,410,605 A 4/1995 Sawada et al.
5,425,105 A 6/1995 Lo et al.
5,445,517 A 8/1995 Kondou et al.
5,465,413 A 11/1995 Enge et al.
5,481,615 A 1/1996 Eatwell et al.
5,548,681 A 8/1996 Gleaves et al.
5,559,893 A * 9/1996 Krokstad ........... G10K 11/1784 381/71.6
5,586,190 A 12/1996 Trantow et al.
5,640,450 A 6/1997 Watanabe
5,668,747 A 9/1997 Ohashi
5,696,831 A 12/1997 Inanaga
5,699,437 A 12/1997 Finn
5,706,344 A 1/1998 Finn
5,740,256 A 4/1998 Castello Da Costa et al.
5,768,124 A 6/1998 Stothers et al.
5,815,582 A 9/1998 Claybaugh et al.
5,832,095 A 11/1998 Daniels
5,909,498 A 6/1999 Smith
5,940,519 A 8/1999 Kuo
5,946,391 A 8/1999 Dragwidge et al.
5,991,418 A 11/1999 Kuo
6,041,126 A 3/2000 Terai et al.
6,118,878 A 9/2000 Jones
6,219,427 B1 4/2001 Kates et al.
6,278,786 B1 8/2001 McIntosh
6,282,176 B1 8/2001 Hemkumar
6,418,228 B1 7/2002 Terai et al.
6,434,246 B1 8/2002 Kates et al.
6,434,247 B1 8/2002 Kates et al.
6,522,746 B1 2/2003 Marchok et al.
6,683,960 B1 1/2004 Fujii et al.
6,766,292 B1 7/2004 Chandran et al.
6,768,795 B2 7/2004 Feltstrom et al.
6,850,617 B1 2/2005 Weigand
6,940,982 B1 9/2005 Watkins
7,058,463 B1 6/2006 Ruha et al.
7,103,188 B1 9/2006 Jones
7,181,030 B2 2/2007 Rasmussen et al.
7,330,739 B2 2/2008 Somayajula
7,365,669 B1 4/2008 Melanson
7,466,838 B1 12/2008 Moseley
7,680,456 B2 3/2010 Muhammad et al.
7,742,790 B2 6/2010 Konchitsky et al.
7,817,808 B2 10/2010 Konchitsky et al.
7,885,417 B2 2/2011 Christoph
8,019,050 B2 9/2011 Mactavish et al.
8,249,262 B2 8/2012 Chua et al.
8,290,537 B2 10/2012 Lee et al.
8,325,934 B2 12/2012 Kuo
8,363,856 B2 1/2013 Lesso et al.
8,379,884 B2 2/2013 Horibe et al.
8,401,200 B2 3/2013 Tiscareno et al.
8,442,251 B2 5/2013 Jensen et al.
8,526,627 B2 9/2013 Asao et al.
8,804,974 B1 8/2014 Melanson
8,848,936 B2 9/2014 Kwatra et al.
8,907,829 B1 12/2014 Naderi
8,908,877 B2 12/2014 Abdollahzadeh Milani et al.
8,948,407 B2 2/2015 Alderson et al.
8,958,571 B2 2/2015 Kwatra et al.
9,066,176 B2 6/2015 Hendrix et al.
9,094,744 B1 7/2015 Lu et al.
9,106,989 B2 8/2015 Li et al.
9,107,010 B2 8/2015 Abdollahzadeh Milani et al.
9,264,808 B2 2/2016 Zhou et al.
2001/0053228 A1 12/2001 Jones
2002/0003887 A1 1/2002 Zhang et al.
2003/0063759 A1 4/2003 Brennan et al.
2003/0072439 A1 4/2003 Gupta
2003/0185403 A1 10/2003 Sibbald
2004/0001450 A1 1/2004 He et al.
2004/0047464 A1 3/2004 Yu et al.
2004/0120535 A1 6/2004 Woods
2004/0165736 A1 8/2004 Hetherington et al.
2004/0167777 A1 8/2004 Hetherington et al.
2004/0176955 A1 9/2004 Farinelli, Jr.
2004/0202333 A1 10/2004 Csermak et al.
2004/0240677 A1 12/2004 Onishi et al.
2004/0242160 A1 12/2004 Ichikawa et al.
2004/0264706 A1 12/2004 Ray et al.
2005/0004796 A1 1/2005 Trump et al.
2005/0018862 A1 1/2005 Fisher
2005/0117754 A1 6/2005 Sakawaki
2005/0207585 A1 9/2005 Christoph
2005/0240401 A1 10/2005 Ebenezer
2006/0035593 A1 2/2006 Leeds
2006/0055910 A1 3/2006 Lee
2006/0069556 A1 3/2006 Nadjar et al.
2006/0109941 A1 5/2006 Keele, Jr.
2006/0153400 A1 7/2006 Fujita et al.
2007/0030989 A1 2/2007 Kates
2007/0033029 A1 2/2007 Sakawaki
2007/0038441 A1 2/2007 Inoue et al.
2007/0047742 A1 3/2007 Taenzer et al.
2007/0053524 A1 3/2007 Haulick et al.
2007/0076896 A1 4/2007 Hosaka et al.
2007/0154031 A1 7/2007 Avendano et al.
2007/0258597 A1 11/2007 Rasmussen et al.
2007/0297620 A1 12/2007 Choy
2008/0019548 A1 1/2008 Avendano
2008/0101589 A1 5/2008 Horowitz et al.
2008/0107281 A1 5/2008 Togami et al.
2008/0144853 A1 6/2008 Sommerfeldt et al.
2008/0166002 A1 7/2008 Amsel
2008/0177532 A1 7/2008 Greiss et al.
2008/0181422 A1 * 7/2008 Christoph .......... G10K 11/1784 381/73.1
2008/0226098 A1 9/2008 Haulick et al.
2008/0240413 A1 10/2008 Mohammad et al.
2008/0240455 A1 10/2008 Inoue et al.
2008/0240457 A1 10/2008 Innoue et al.
2009/0012783 A1 1/2009 Klein
2009/0034748 A1 2/2009 Sibbald
2009/0041260 A1 2/2009 Jorgensen et al.
2009/0046867 A1 2/2009 Clemow
2009/0060222 A1 3/2009 Jeong et al.
2009/0080670 A1 3/2009 Solbeck et al.
2009/0086990 A1 4/2009 Christoph
2009/0136057 A1 5/2009 Taenzer
2009/0175461 A1 7/2009 Nakamura et al.
2009/0175466 A1 7/2009 Elko et al.
2009/0196429 A1 8/2009 Ramakrishnan et al.
2009/0220107 A1 9/2009 Every et al.
2009/0238369 A1 9/2009 Ramakrishnan et al.
2009/0245529 A1 10/2009 Asada et al.
2009/0254340 A1 10/2009 Sun et al.
2009/0290718 A1 11/2009 Kahn et al.
2009/0296965 A1 12/2009 Kojima
2009/0304200 A1 12/2009 Kim et al.
2009/0311979 A1 12/2009 Husted et al.
2010/0014683 A1 1/2010 Maeda et al.
2010/0014685 A1 1/2010 Wurm
2010/0061564 A1 3/2010 Clemow et al.
2010/0069114 A1 3/2010 Lee et al.
2010/0082339 A1 4/2010 Konchitsky et al.
2010/0098263 A1 4/2010 Pan et al.
2010/0098265 A1 4/2010 Pan et al.
2010/0124336 A1 5/2010 Shridhar et al.
2010/0124337 A1 5/2010 Wertz et al.
2010/0131269 A1 5/2010 Park et al.
2010/0142715 A1 6/2010 Goldstein et al.
2010/0150367 A1 6/2010 Mizuno
2010/0158330 A1 6/2010 Guissin et al.

(56) References Cited

U.S. PATENT DOCUMENTS

2010/0166203 A1 7/2010 Peissig et al.
2010/0183175 A1 7/2010 Chen et al.
2010/0195838 A1 8/2010 Bright
2010/0195844 A1 8/2010 Christoph et al.
2010/0207317 A1 8/2010 Iwami et al.
2010/0246855 A1 9/2010 Chen
2010/0266137 A1 10/2010 Sibbald et al.
2010/0272276 A1 10/2010 Carreras et al.
2010/0272283 A1 10/2010 Carreras et al.
2010/0272284 A1 10/2010 Marcel et al.
2010/0274564 A1 10/2010 Bakalos et al.
2010/0284546 A1 11/2010 DeBrunner et al.
2010/0291891 A1 11/2010 Ridgers et al.
2010/0296666 A1 11/2010 Lin
2010/0296668 A1 11/2010 Lee et al.
2010/0310086 A1 12/2010 Magrath et al.
2010/0310087 A1 12/2010 Ishida
2010/0316225 A1 12/2010 Saito et al.
2010/0322430 A1 12/2010 Isberg
2011/0002468 A1 1/2011 Tanghe
2011/0007907 A1 1/2011 Park et al.
2011/0026724 A1 2/2011 Doclo
2011/0096933 A1 4/2011 Eastty
2011/0106533 A1 5/2011 Yu
2011/0116643 A1* 5/2011 Tiscareno ............ H04R 1/1016 381/58
2011/0129098 A1 6/2011 Delano et al.
2011/0130176 A1 6/2011 Magrath et al.
2011/0142247 A1 6/2011 Fellers et al.
2011/0144984 A1 6/2011 Konchitsky
2011/0150257 A1 6/2011 Jensen
2011/0158419 A1 6/2011 Theverapperuma et al.
2011/0206214 A1 8/2011 Christoph et al.
2011/0222698 A1 9/2011 Asao et al.
2011/0222701 A1 9/2011 Donaldson
2011/0249826 A1 10/2011 Van Leest
2011/0288860 A1 11/2011 Schevciw et al.
2011/0293103 A1 12/2011 Park et al.
2011/0299695 A1 12/2011 Nicholson
2011/0305347 A1* 12/2011 Wurm .................. G10K 11/178 381/71.1
2011/0317848 A1 12/2011 Ivanov et al.
2012/0057720 A1 3/2012 Van Leest
2012/0084080 A1 4/2012 Konchitsky et al.
2012/0135787 A1 5/2012 Kusunoki et al.
2012/0140917 A1 6/2012 Nicholson et al.
2012/0140942 A1 6/2012 Loeda
2012/0140943 A1 6/2012 Hendrix et al.
2012/0148062 A1 6/2012 Scarlett et al.
2012/0155666 A1 6/2012 Nair
2012/0170766 A1 7/2012 Alves et al.
2012/0185524 A1 7/2012 Clark
2012/0207317 A1 8/2012 Abdollahzadeh Milani et al.
2012/0215519 A1 8/2012 Park et al.
2012/0250873 A1 10/2012 Bakalos et al.
2012/0259626 A1 10/2012 Li et al.
2012/0263317 A1 10/2012 Shin et al.
2012/0281850 A1 11/2012 Hyatt
2012/0300958 A1 11/2012 Klemmensen
2012/0300960 A1 11/2012 Mackay et al.
2012/0308021 A1 12/2012 Kwatra et al.
2012/0308024 A1 12/2012 Alderson et al.
2012/0308025 A1 12/2012 Hendrix et al.
2012/0308026 A1 12/2012 Kamath et al.
2012/0308027 A1 12/2012 Kwatra
2012/0308028 A1 12/2012 Kwatra et al.
2012/0310640 A1 12/2012 Kwatra et al.
2013/0010982 A1 1/2013 Elko et al.
2013/0083939 A1 4/2013 Fellers et al.
2013/0156238 A1 6/2013 Birch et al.
2013/0222516 A1 8/2013 Do et al.
2013/0243198 A1 9/2013 Van Rumpt
2013/0243225 A1 9/2013 Yokota
2013/0259251 A1 10/2013 Bakalos
2013/0272539 A1 10/2013 Kim et al.
2013/0287218 A1 10/2013 Alderson et al.
2013/0287219 A1 10/2013 Hendrix et al.
2013/0301842 A1 11/2013 Hendrix et al.
2013/0301846 A1 11/2013 Alderson et al.
2013/0301847 A1 11/2013 Alderson et al.
2013/0301848 A1 11/2013 Zhou et al.
2013/0301849 A1 11/2013 Alderson et al.
2013/0315403 A1 11/2013 Samuelsson
2013/0343556 A1 12/2013 Bright
2013/0343571 A1 12/2013 Rayala et al.
2014/0036127 A1 2/2014 Pong et al.
2014/0044275 A1 2/2014 Goldstein et al.
2014/0050332 A1 2/2014 Nielsen et al.
2014/0051483 A1* 2/2014 Schoerkmaier .... G10K 11/1784 455/570
2014/0072134 A1 3/2014 Po et al.
2014/0072135 A1 3/2014 Bajic et al.
2014/0086425 A1 3/2014 Jensen et al.
2014/0126735 A1 5/2014 Gauger, Jr.
2014/0169579 A1 6/2014 Azmi
2014/0177851 A1 6/2014 Kitazawa et al.
2014/0177890 A1 6/2014 Hojlund et al.
2014/0211953 A1 7/2014 Alderson et al.
2014/0226827 A1 8/2014 Abdollahzadeh Milani et al.
2014/0270222 A1 9/2014 Hendrix et al.
2014/0270223 A1 9/2014 Li et al.
2014/0270224 A1 9/2014 Zhou et al.
2014/0294182 A1 10/2014 Axelsson
2014/0307887 A1 10/2014 Alderson et al.
2014/0307888 A1 10/2014 Alderson et al.
2014/0307890 A1 10/2014 Zhou et al.
2014/0307899 A1 10/2014 Hendrix et al.
2014/0314244 A1 10/2014 Yong et al.
2014/0314246 A1 10/2014 Hellman
2014/0314247 A1 10/2014 Zhang
2014/0369517 A1 12/2014 Zhou et al.
2015/0078572 A1 3/2015 Abdollahzadeh Milani
2015/0092953 A1 4/2015 Abdollahzadeh Milani et al.
2015/0104032 A1 4/2015 Kwatra et al.
2015/0161980 A1 6/2015 Alderson et al.
2015/0161981 A1 6/2015 Kwatra
2015/0163592 A1 6/2015 Alderson
2015/0256660 A1 9/2015 Kaller et al.
2015/0256953 A1 9/2015 Kwatra et al.
2015/0269926 A1 9/2015 Alderson et al.
2015/0365761 A1 12/2015 Alderson et al.

FOREIGN PATENT DOCUMENTS

EP 0412902 A2 2/1991
EP 0756407 A2 1/1997
EP 1691577 A2 8/2006
EP 1880699 A2 1/2008
EP 1947642 A1 7/2008
EP 2133866 A1 12/2009
EP 2237573 A1 10/2010
EP 2216774 A1 8/2011
EP 2395500 A1 12/2011
EP 2395501 A1 12/2011
EP 2551845 A1 1/2013
EP 2583074 A1 4/2013
GB 2401744 A 11/2004
GB 2436657 A 10/2007
GB 2455821 A 6/2009
GB 2455824 A 6/2009
GB 2455828 A 6/2009
GB 2484722 A 4/2012
JP H06186985 A 7/1994
JP H06232755 8/1994
JP 07325588 A 12/1995
JP 2000089770 3/2000
JP 2004007107 1/2004
JP 2007060644 3/2007
JP 2010277025 12/2010
JP 2011061449 3/2011
WO 9911045 3/1999
WO 03015074 A1 2/2003
WO 03015275 A1 2/2003
WO WO2004009007 A1 1/2004

(56) References Cited

FOREIGN PATENT DOCUMENTS

| | | | |
|---|---|---|---|
| WO | 2004017303 | A1 | 2/2004 |
| WO | 2006128768 | A1 | 12/2006 |
| WO | 2007007916 | A1 | 1/2007 |
| WO | 2007011337 | A1 | 1/2007 |
| WO | 2007110807 | A2 | 10/2007 |
| WO | 2007113487 | A1 | 11/2007 |
| WO | 2009041012 | A1 | 4/2009 |
| WO | 2009110087 | A1 | 9/2009 |
| WO | 2010117714 | A1 | 10/2010 |
| WO | 2011035061 | A1 | 3/2011 |
| WO | 2012107561 | A1 | 8/2012 |
| WO | 2012119808 | A2 | 9/2012 |
| WO | 2012134874 | A1 | 10/2012 |
| WO | 2012166273 | A2 | 12/2012 |
| WO | 2012166388 | A2 | 12/2012 |
| WO | 2014158475 | A1 | 10/2014 |
| WO | 2014168685 | A2 | 10/2014 |
| WO | 2014172005 | A1 | 10/2014 |
| WO | 2014172006 | A1 | 10/2014 |
| WO | 2014172010 | A1 | 10/2014 |
| WO | 2014172019 | A1 | 10/2014 |
| WO | 2014172021 | A1 | 10/2014 |
| WO | 2014200787 | A1 | 12/2014 |
| WO | 2015038255 | A1 | 3/2015 |
| WO | 2015088639 | A | 6/2015 |
| WO | 2015088651 | A1 | 6/2015 |
| WO | 2015088653 | A1 | 6/2015 |
| WO | 2015134225 | A1 | 9/2015 |
| WO | 2015191691 | A1 | 12/2015 |

OTHER PUBLICATIONS

Morgan, Dennis R. et al., A Delayless Subband Adaptive Filter Architecture, IEEE Transactions on Signal Processing, IEEE Service Center, New York, NY, U.S., vol. 43, No. 8, Aug. 1995, pp. 1819-1829.

International Patent Application No. PCT/US2014/040999, International Search Report and Written Opinion, Oct. 18, 2014, 12 pages.

International Patent Application No. PCT/US2013/049407, International Search Report and Written Opinion, Jun. 18, 2014, 13 pages.

Ray, Laura et al., Hybrid Feedforward-Feedback Active Noise Reduction for Hearing Protection and Communication, The Journal of the Acoustical Society of America, American Institute of Physics for the Acoustical Society of America, New York, NY, vol. 120, No. 4, Jan. 2006, pp. 2026-2036.

International Patent Application No. PCT/US2014/017112, International Search Report and Written Opinion, May 8, 2015, 22 pages.

International Patent Application No. PCT/US2015/017124, International Search Report and Written Opinion, Jul. 13, 2015, 19 pages.

International Patent Application No. PCT/US2015/035073, International Search Report and Written Opinion, Oct. 8, 2015, 11 pages.

Campbell, Mikey, "Apple looking into self-adjusting earbud headphones with noise cancellation tech", Apple Insider, Jul. 4, 2013, pp. 1-10 (10 pages in pdf), downloaded May 14, 2014 from http://appleinsider.com/articles/13/07/04/apple-looking-into-self-adjusting-earbud-headphones-with-noise-cancellation-tech.

International Patent Application No. PCT/US2014/017096, International Search Report and Written Opinion, May 27, 2014, 11 pages.

International Patent Application No. PCT/US2014/049600, International Search Report and Written Opinion, Jan. 14, 2015, 12 pages.

International Patent Application No. PCT/US2014/061753, International Search Report and Written Opinion, Feb. 9, 2015, 8 pages.

International Patent Application No. PCT/US2014/061548, International Search Report and Written Opinion, Feb. 12, 2015, 13 pages.

International Patent Application No. PCT/US2014/060277, International Search Report and Written Opinion, Mar. 9, 2015, 11 pages.

Kou, Sen and Tsai, Jianming, Residual noise shaping technique for active noise control systems, J. Acoust. Soc. Am. 95 (3), Mar. 1994, pp. 1665-1668.

Pfann, et al., "LMS Adaptive Filtering with Delta-Sigma Modulated Input Signals," IEEE Signal Processing Letters, Apr. 1998, pp. 95-97, vol. 5, No. 4, IEEE Press, Piscataway, NJ.

Toochinda, et al., "A Single-Input Two-Output Feedback Formulation for ANC Problems," Proceedings of the 2001 American Control Conference, Jun. 2001, pp. 923-928, vol. 2, Arlington, VA.

Kuo, et al., "Active Noise Control: A Tutorial Review," Proceedings of the IEEE, Jun. 1999, pp. 943-973, vol. 87, No. 6, IEEE Press, Piscataway, NJ.

Johns, et al., "Continuous-Time LMS Adaptive Recursive Filters," IEEE Transactions on Circuits and Systems, Jul. 1991, pp. 769-778, vol. 38, No. 7, IEEE Press, Piscataway, NJ.

Shoval, et al., "Comparison of DC Offset Effects in Four LMS Adaptive Algorithms," IEEE Transactions on Circuits and Systems II: Analog and Digital Processing, Mar. 1995, pp. 176-185, vol. 42, Issue 3, IEEE Press, Piscataway, NJ.

Mali, Dilip, "Comparison of DC Offset Effects on LMB Algorithm and its Derivatives," International Journal of Recent Trends in Engineering, May 2009, pp. 323-328, vol. 1, No. 1, Academy Publisher.

Kates, James M., "Principles of Digital Dynamic Range Compression," Trends in Amplification, Spring 2005, pp. 45-76, vol. 9, No. 2, Sage Publications.

Gao, et al., "Adaptive Linearization of a Loudspeaker," IEEE International Conference on Acoustics, Speech, and Signal Processing, Apr. 14-17, 1991, pp. 3589-3592, Toronto, Ontario, CA.

Silva, et al., "Convex Combination of Adaptive Filters With Different Tracking Capabilities," IEEE International Conference on Acoustics, Speech, and Signal Processing, Apr. 15-20, 2007, pp. III 925-928, vol. 3, Honolulu, HI, USA.

Akhtar, et al., "A Method for Online Secondary Path Modeling in Active Noise Control Systems," IEEE International Symposium on Circuits and Systems, May 23-26, 2005, p. 264-267, vol. 1, Kobe, Japan.

Davari, et al., "A New Online Secondary Path Modeling Method for Feedforward Active Noise Control Systems," IEEE International Conference on Industrial Technology, Apr. 21-24, 2008, pp. 1-6, Chengdu, China.

Lan, et al., "An Active Noise Control System Using Online Secondary Path Modeling With Reduced Auxiliary Noise," IEEE Signal Processing Letters, Jan. 2002, p. 16-18, vol. 9, Issue 1, IEEE Press, Piscataway, NJ.

Liu, et al., "Analysis of Online Secondary Path Modeling With Auxiliary Noise Scaled by Residual Noise Signal," IEEE Transactions on Audio, Speech and Language Processing, Nov. 2010, p. 1978-1993, vol. 18, Issue 8, IEEE Press, Piscataway, NJ.

Booji, P.S., Berkhoff, A.P., Virtual sensors for local, three dimensional, broadband multiple-channel active noise control and the effects on the quiet zones, Proceedings of ISMA2010 including USD2010, pp. 151-166.

Lopez-Caudana, Edgar Omar, Active Noise Cancellation: The Unwanted Signal and the Hybrid Solution, Adaptive Filtering Applications, Dr. Lino Garcia, ISBN: 978-953-307-306-4, InTech.

D. Senderowicz et al., "Low-Voltage Double-Sampled Delta-Sigma Converters," IEEE J. Solid-State Circuits, vol. 32 No. 12, pp. 1907-1919, Dec. 1997, 13 pages.

Hurst, P.J. and Dyer, K.C., "An improved double sampling scheme for switched-capacitor delta-sigma modulators," IEEE Int. Symp. Circuits Systems, May 1992, vol. 3, pp. 1179-1182, 4 pages.

Milani, et al., "On Maximum Achievable Noise Reduction in ANC Systems", Proceedings of the IEEE International Conference on Acoustics, Speech, and Signal Processing, ICASSP 2010, Mar. 14-19, 2010 pp. 349-352.

Ryan, et al., "Optimum near-field performance of microphone arrays subject to a far-field beampattern constraint", 2248 J. Acoust. Soc. Am. 108, Nov. 2000.

(56) References Cited

OTHER PUBLICATIONS

Cohen, et al., "Noise Estimation by Minima Controlled Recursive Averaging for Robust Speech Enhancement", IEEE Signal Processing Letters, vol. 9, No. 1, Jan. 2002.
Martin, "Noise Power Spectral Density Estimation Based on Optimal Smoothing and Minimum Statistics", IEEE Trans. on Speech and Audio Processing, Col. 9, No. 5, Jul. 2001.
Martin, "Spectral Subtraction Based on Minimum Statistics", Proc. 7th EUSIPCO '94, Edinburgh, U.K., Sep. 13-16, 1994, pp. 1182-1195.
Cohen, "Noise Spectrum Estimation in Adverse Environments: Improved Minima Controlled Recursive Averaging", IEEE Trans. on Speech & Audio Proc., vol. 11, Issue 5, Sep. 2003.
Black, John W., "An Application of Side-Tone in Subjective Tests of Microphones and Headsets", Project Report No. NM 001 064. 01.20, Research Report of the U.S. Naval School of Aviation Medicine, Feb. 1, 1954, 12 pages. (pp. 1-12 in pdf), Pensacola, FL, US.
Lane, et al., "Voice Level: Autophonic Scale, Perceived Loudness, and the Effects of Sidetone", The Journal of the Acoustical Society of America, Feb. 1961, pp. 160-167, vol. 33, No. 2., Cambridge, MA, US.
Liu, et al., "Compensatory Responses to Loudness-shifted Voice Feedback During Production of Mandarin Speech", Journal of the Acoustical Society of America, Oct. 2007, pp. 2405-2412, vol. 122, No. 4.
Paepcke, et al., "Yelling in the Hall: Using Sidetone to Address a Problem with Mobile Remote Presence Systems", Symposium on User Interface Software and Technology, Oct. 16-19, 2011, 10 pages (pp. 1-10 in pdf), Santa Barbara, CA, US.
Peters, Robert W., "The Effect of High-Pass and Low-Pass Filtering of Side-Tone Upon Speaker Intelligibility", Project Report No. NM 001 064.01.25, Research Report of the U.S. Naval School of Aviation Medicine, Aug. 16, 1954, 13 pages (pp. 1-13 in pdf), Pensacola, FL, US.
Therrien, et al., "Sensory Attenuation of Self-Produced Feedback: The Lombard Effect Revisited", PLOS ONE, Nov. 2012, pp. 1-7, vol. 7, Issue 11, e49370, Ontario, Canada.
Jin, et al., "A simultaneous equation method-based online secondary path modeling algorithm for active noise control", Journal of Sound and Vibration, Apr. 25, 2007, pp. 455-474, vol. 303, No. 3-5, London, GB.
Erkelens et al., "Tracking of Nonstationary Noise Based on Data-Driven Recursive Noise Power Estimation", IEEE Transactions on Audio Speech, and Language Processing, vol. 16, No. 6, Aug. 2008.
Rao et al., "A Novel Two Stage Single Channle Speech Enhancement Technique", India Conference (INDICON) 2011 Annual IEEE, IEEE, Dec. 15, 2011.
Rangachari et al., "A noise-estimation algorithm for highly non-stationary environments" Speech Communication, Elsevier Science Publishers, vol. 48, No. 2, Feb. 1, 2006.
International Search Report and Written Opinion of the International Searching Authority, International Patent Application No. PCT/US2014/017343, mailed Aug. 8, 2014, 22 pages.
International Search Report and Written Opinion of the International Searching Authority, International Patent Application No. PCT/US2014/018027, mailed Sep. 4, 2014, 14 pages.
International Search Report and Written Opinion of the International Searching Authority, International Patent Application No. PCT/US2014/017374, mailed Sep. 8, 2014, 13 pages.
International Search Report and Written Opinion of the International Searching Authority, International Patent Application No. PCT/US2014/019395, mailed Sep. 9, 2014, 14 pages.
International Search Report and Written Opinion of the International Searching Authority, International Patent Application No. PCT/US2014/019469, mailed Sep. 12, 2014, 13 pages.
Feng, Jinwei et al., "A broadband self-tuning active noise equaliser", Signal Processing, Elsevier Science Publishers B.V. Amsterdam, NL, vol. 62, No. 2, Oct. 1, 1997, pp. 251-256.
Zhang, Ming et al., "A Robust Online Secondary Path Modeling Method with Auxiliary Noise Power Scheduling Strategy and Norm Constraint Manipulation", IEEE Transactions on Speech and Audio Processing, IEEE Service Center, New York, NY, vol. 11, No. 1, Jan. 1, 2003.
Lopez-Gaudana, Edgar et al., "A hybrid active noise cancelling with secondary path modeling", 51st Midwest Symposium on Circuits and Systems, 2008, MWSCAS 2008, Aug. 10, 2008, pp. 277-280.
Parkins, et al., Narrowband and broadband active control in an enclosure using the acoustic energy density, J. Acoust. Soc. Am. Jul. 2000, pp. 192-203, vol. 108, issue 1, U.S.
International Patent Application No. PCT/US2015/022113, International Search Report and Written Opinion, Jul. 23, 2015, 13 pages.
Combined Search and Examination Report, Application No. GB1512832.5, mailed Jan. 28, 2016, 7 pages.
Combined Search and Examination Report, Application No. GB1519000.2, Mailed Apr. 21, 2016, 5 pages.
International Patent Application No. PCT/US2015/066260, International Search Report and Written Opinion, mailed Apr. 21, 2016, 13 pages.

* cited by examiner

SYSTEMS AND METHODS FOR ADAPTIVE NOISE CANCELLATION BY BIASING ANTI-NOISE LEVEL

RELATED APPLICATION

The present disclosure claims priority to U.S. Provisional Patent Application Ser. No. 61/812,842, filed Apr. 17, 2013, which is incorporated by reference herein in its entirety.

FIELD OF DISCLOSURE

The present disclosure relates in general to adaptive noise cancellation in connection with an acoustic transducer, and more particularly, to detection and cancellation of ambient noise present in the vicinity of the acoustic transducer, including biasing an anti-noise level for anti-noise generated by adaptive noise cancellation.

BACKGROUND

Wireless telephones, such as mobile/cellular telephones, cordless telephones, and other consumer audio devices, such as mp3 players, are in widespread use. Performance of such devices with respect to intelligibility can be improved by providing noise canceling using a microphone to measure ambient acoustic events and then using signal processing to insert an anti-noise signal into the output of the device to cancel the ambient acoustic events.

Because the acoustic environment around personal audio devices, such as wireless telephones, can change dramatically, depending on the sources of noise that are present and the position of the device itself, it is desirable to adapt the noise canceling to take into account such environmental changes. For example, many adaptive noise cancelling systems utilize an error microphone for sensing acoustic pressure proximate to an output of an electro-acoustic transducer (e.g., a loudspeaker) and generating an error microphone signal indicative of the acoustic output of the transducer and the ambient audio sounds at the transducer. When the transducer is close to a listener's ear, the error microphone signal may approximate the actual acoustic pressure at a listener's eardrum (a location known as a drum reference point). However, because of the distance between the drum reference point and the location of the error microphone (known as the error reference point) the error microphone signal is only an approximation and not a perfect indication of acoustic pressure at the drum reference point. Thus, because noise cancellation attempts to reduce ambient audio sounds present in the error microphone signal, performance of a noise cancellation system may be the greatest when the distance between the drum reference point and the error reference point is small. As the distance increases (e.g., transducer held against the ear at a lower pressure), the performance of the noise cancellation system may degrade, partly because the gain of the transfer function from the error reference point to the drum reference point decreases with such increased distance. This degradation is not accounted for in traditional adaptive noise cancellation systems.

SUMMARY

In accordance with the teachings of the present disclosure, the disadvantages and problems associated with existing approaches to adaptive noise cancellation may be reduced or eliminated.

In accordance with embodiments of the present disclosure, a personal audio device may include a personal audio device housing, a transducer, a reference microphone, an error microphone, and a processing circuit. The transducer may be mounted on the housing and may be configured to reproduce an audio signal including both a source audio signal for playback to a listener and an anti-noise signal for countering the effects of ambient audio sounds in an acoustic output of the transducer. The reference microphone may be mounted on the housing and may be configured to provide a reference microphone signal indicative of the ambient audio sounds. The error microphone may be mounted on the housing in proximity to the transducer and may be configured to provide an error microphone signal indicative of the acoustic output of the transducer and the ambient audio sounds at the transducer. The processing circuit may comprise an adaptive filter having a response that generates an anti-noise signal from the reference microphone signal, a secondary path estimate filter configured to model an electro-acoustic path of the source audio signal having a response that generates a secondary path estimate from the source audio, a biasing portion that generates a scaled anti-noise signal by applying a scaling factor and the response of the secondary path estimate filter to the anti-noise signal, and a coefficient control block that shapes the response of the adaptive filter in conformity with the reference microphone signal and a modified playback corrected error signal by adapting the response of the adaptive filter to minimize the ambient audio sounds in the error microphone signal, wherein the playback corrected error is based on a difference between the error microphone signal and the source audio signal and the modified playback corrected error signal is based on a difference between the playback corrected error signal and the scaled anti-noise signal.

In accordance with these and other embodiments of the present disclosure, a method for canceling ambient audio sounds in the proximity of a transducer of a personal audio device may include measuring ambient audio sounds with a reference microphone to produce a reference microphone signal. The method may also include measuring an output of the transducer and the ambient audio sounds at the transducer with an error microphone to produce an error microphone signal. The method may additionally include generating a source audio signal for playback to a listener. The method may also include adaptively generating an anti-noise signal, from a result of the measuring with the reference microphone, countering the effects of ambient audio sounds at an acoustic output of the transducer by adapting a response of an adaptive filter that filters the reference microphone signal in conformity with the reference microphone signal and a modified playback corrected error signal to minimize the ambient audio sounds in the error microphone. The method may also include generating a secondary path estimate from the source audio signal by filtering the source audio signal with a secondary path estimate filter modeling an electro-acoustic path of the source audio signal. The method may additionally include generating a scaled anti-noise signal by applying a scaling factor and the response of the secondary path estimate filter to the anti-noise signal. The method may further include combining the anti-noise signal with a source audio signal to generate an audio signal provided to the transducer. The playback corrected error may be based on a difference between the error microphone signal and the source audio signal and the modified playback corrected error signal may be based on a difference between the playback corrected error signal and the scaled anti-noise signal.

In accordance with these and other embodiments of the present disclosure, an integrated circuit for implementing at least a portion of a personal audio device may include an output, a reference microphone input, an error microphone input, and a processing circuit. The output may be configured to provide a signal to a transducer including both a source audio signal for playback to a listener and an anti-noise signal for countering the effect of ambient audio sounds in an acoustic output of the transducer. The reference microphone input may be configured to receive a reference microphone signal indicative of the ambient audio sounds. The error microphone input may be configured to receive an error microphone signal indicative of the output of the transducer and the ambient audio sounds at the transducer. The processing circuit may comprise an adaptive filter having a response that generates an anti-noise signal from the reference microphone signal, a secondary path estimate filter configured to model an electro-acoustic path of the source audio signal having a response that generates a secondary path estimate from the source audio, a biasing portion that generates a scaled anti-noise signal by applying a scaling factor and the response of the secondary path estimate filter to the anti-noise signal, and a coefficient control block that shapes the response of the adaptive filter in conformity with the reference microphone signal and a modified playback corrected error signal by adapting the response of the adaptive filter to minimize the ambient audio sounds in the error microphone signal, wherein the playback corrected error is based on a difference between the error microphone signal and the source audio signal and the modified playback corrected error signal is based on a difference between the playback corrected error signal and the scaled anti-noise signal.

Technical advantages of the present disclosure may be readily apparent to one skilled in the art from the figures, description and claims included herein. The objects and advantages of the embodiments will be realized and achieved at least by the elements, features, and combinations particularly pointed out in the claims.

It is to be understood that both the foregoing general description and the following detailed description are examples and explanatory and are not restrictive of the claims set forth in this disclosure.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

The present disclosure encompasses noise canceling techniques and circuits that can be implemented in a personal audio device, such as a wireless telephone. The personal audio device includes an ANC circuit that may measure the ambient acoustic environment and generate a signal that is injected in the speaker (or other transducer) output to cancel ambient acoustic events. A reference microphone may be provided to measure the ambient acoustic environment and an error microphone may be included for controlling the adaptation of the anti-noise signal to cancel the ambient audio sounds and for correcting for the electro-acoustic path from the output of the processing circuit through the transducer.

Figure 1:
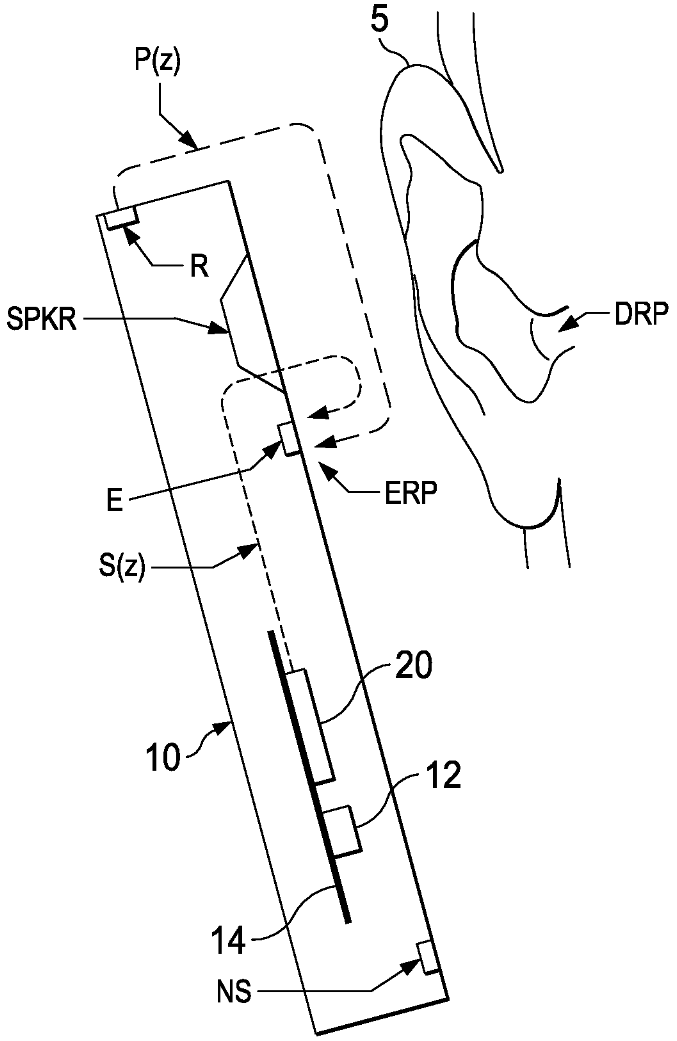
FIG. 1 is an illustration of an example wireless mobile telephone, in accordance with embodiments of the present disclosure.

Referring now to FIG. 1, a wireless telephone 10 as illustrated in accordance with embodiments of the present disclosure is shown in proximity to a human ear 5. Wireless telephone 10 is an example of a device in which techniques in accordance with embodiments of the invention may be employed, but it is understood that not all of the elements or configurations embodied in illustrated wireless telephone 10, or in the circuits depicted in subsequent illustrations, are required in order to practice the inventions recited in the claims. Wireless telephone 10 may include a transducer such as speaker SPKR that reproduces distant speech received by wireless telephone 10, along with other local audio events such as ringtones, stored audio program material, injection of near-end speech (i.e., the speech of the user of wireless telephone 10) to provide a balanced conversational perception, and other audio that requires reproduction by wireless telephone 10, such as sources from webpages or other network communications received by wireless telephone 10 and audio indications such as a low battery indication and other system event notifications. A near-speech microphone NS may be provided to capture near-end speech, which is transmitted from wireless telephone 10 to the other conversation participant(s).

Wireless telephone 10 may include ANC circuits and features that inject an anti-noise signal into speaker SPKR to improve intelligibility of the distant speech and other audio reproduced by speaker SPKR. A reference microphone R may be provided for measuring the ambient acoustic environment, and may be positioned away from the typical position of a user's mouth, so that the near-end speech may be minimized in the signal produced by reference microphone R. Another microphone, error microphone E, may be provided in order to further improve the ANC operation by providing a measure of the ambient audio combined with the audio reproduced by speaker SPKR close to ear 5 at an error microphone reference position ERP, when wireless telephone 10 is in close proximity to ear 5. In different embodiments, additional reference and/or error microphones may be employed. Circuit 14 within wireless telephone 10 may include an audio CODEC integrated circuit (IC) 20 that receives the signals from reference microphone R, near-speech microphone NS, and error microphone E, and interfaces with other integrated circuits such as a radio-frequency (RF) integrated circuit 12 having a wireless telephone transceiver. In some embodiments of the disclosure, the circuits and techniques disclosed herein may be incorporated in a single integrated circuit that includes control circuits and other functionality for implementing the entirety of the personal audio device, such as an MP3 player-on-a-chip integrated circuit. In these and other embodiments, the circuits and techniques disclosed herein may be implemented partially or fully in software and/or firmware embodied in computer-readable media and executable by a controller or other processing device.

In general, ANC techniques of the present disclosure measure ambient acoustic events (as opposed to the output of speaker SPKR and/or the near-end speech) impinging on reference microphone R, and by also measuring the same ambient acoustic events impinging on error microphone E, ANC processing circuits of wireless telephone 10 adapt an anti-noise signal generated from the output of reference microphone R to have a characteristic that minimizes the amplitude of the ambient acoustic events at error microphone E (e.g., at error microphone reference position ERP). Because acoustic path P(z) extends from reference microphone R to error microphone E, ANC circuits are effectively estimating acoustic path P(z) while removing effects of an electro-acoustic path S(z) that represents the response of the audio output circuits of CODEC IC 20 and the acoustic/electric transfer function of speaker SPKR including the coupling between speaker SPKR and error microphone E in the particular acoustic environment, which may be affected by the proximity and structure of ear 5 and other physical objects and human head structures that may be in proximity to wireless telephone 10, when wireless telephone 10 is not firmly pressed to ear 5. Because the listener of wireless telephone actually hears the output of speaker SPKR at a drum reference point DRP, differences between the error microphone reference signal produced by error microphone E and what is actually heard by the listener are shaped at least by the response of the ear canal, as well as a spatial distance between error microphone reference position ERP and drum reference position DRP.

While the illustrated wireless telephone 10 includes a two-microphone ANC system with a third near-speech microphone NS, some aspects of the present invention may be practiced in a system that does not include separate error and reference microphones, or a wireless telephone that uses near-speech microphone NS to perform the function of the reference microphone R. Also, in personal audio devices designed only for audio playback, near-speech microphone NS will generally not be included, and the near-speech signal paths in the circuits described in further detail below may be omitted, without changing the scope of the disclosure.

Figure 2:
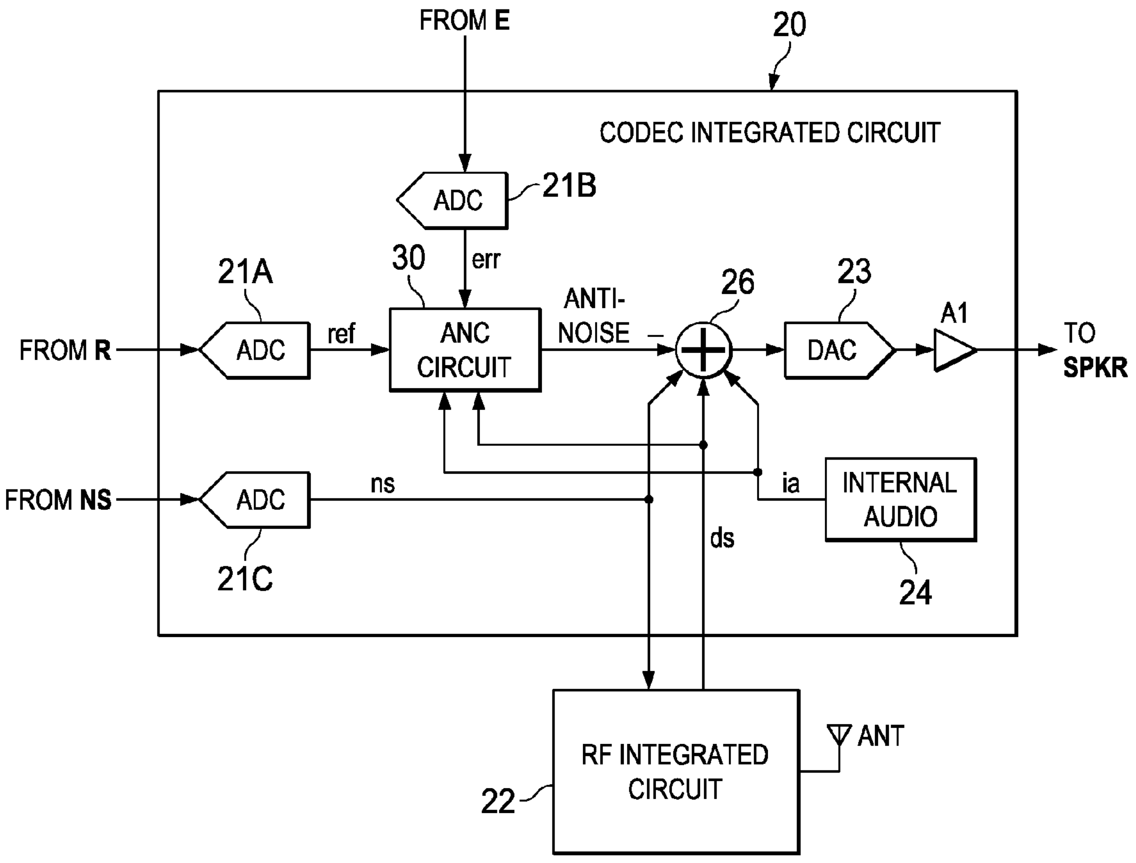
FIG. 2 is a block diagram of selected circuits within the wireless telephone depicted in FIG. 1, in accordance with embodiments of the present disclosure.

Referring now to FIG. 2, selected circuits within wireless telephone 10 are shown in a block diagram. CODEC IC 20 may include an analog-to-digital converter (ADC) 21A for receiving the reference microphone signal and generating a digital representation ref of the reference microphone signal, an ADC 21B for receiving the error microphone signal and generating a digital representation err of the error microphone signal, and an ADC 21C for receiving the near speech microphone signal and generating a digital representation ns of the near speech microphone signal. CODEC IC 20 may generate an output for driving speaker SPKR from an amplifier A1, which may amplify the output of a digital-to-analog converter (DAC) 23 that receives the output of a combiner 26. Combiner 26 may combine audio signals is from internal audio sources 24, the anti-noise signal generated by ANC circuit 30, which by convention has the same polarity as the noise in reference microphone signal ref and is therefore subtracted by combiner 26, and a portion of near speech microphone signal ns so that the user of wireless telephone 10 may hear his or her own voice in proper relation to downlink speech ds, which may be received from radio frequency (RF) integrated circuit 22 and may also be combined by combiner 26. Near speech microphone signal ns may also be provided to RF integrated circuit 22 and may be transmitted as uplink speech to the service provider via antenna ANT.

Figure 3:
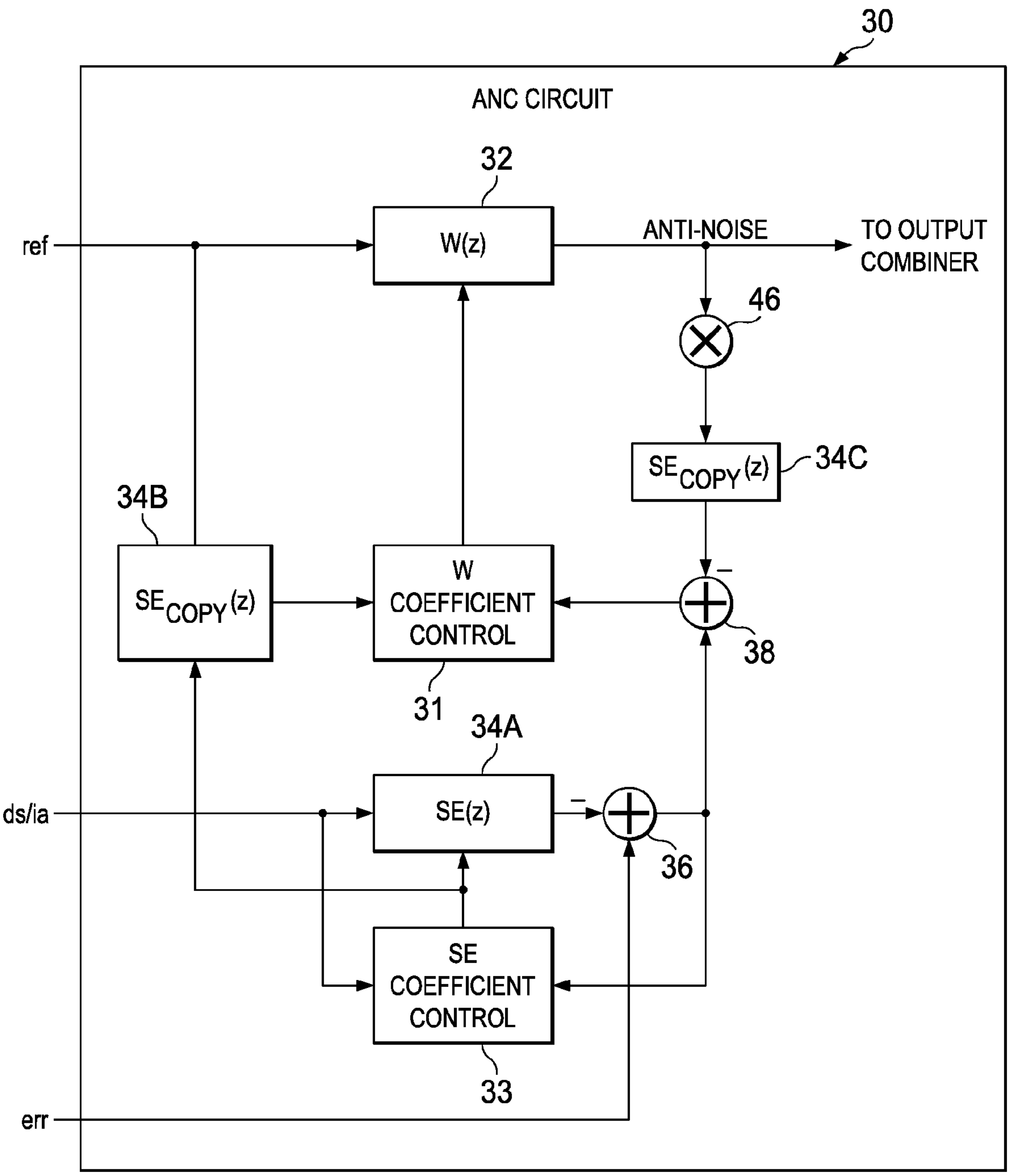
FIG. 3 is a block diagram depicting selected signal processing circuits and functional blocks within an example adaptive noise canceling (ANC) circuit of a coder-decoder (CODEC) integrated circuit of FIG. 3, in accordance with embodiments of the present disclosure.

Referring now to FIG. 3, details of ANC circuit 30 are shown in accordance with embodiments of the present disclosure. Adaptive filter 32 may receive reference microphone signal ref and under ideal circumstances, may adapt its transfer function W(z) to be P(z)/S(z) to generate the anti-noise signal, which may be provided to an output combiner that combines the anti-noise signal with the audio to be reproduced by the transducer, as exemplified by combiner 26 of FIG. 2. The coefficients of adaptive filter 32 may be controlled by a W coefficient control block 31 that uses a correlation of signals to determine the response of adaptive filter 32, which generally minimizes the error, in a least-mean squares sense, between those components of reference microphone signal ref present in error microphone signal err. The signals compared by W coefficient control block 31 may be the reference microphone signal ref as shaped by a copy of an estimate of the response of path S(z) provided by filter 34B and a modified playback corrected error based at least in part on error microphone signal err. The modified playback corrected error may be generated as described in greater detail below.

By transforming reference microphone signal ref with a copy of the estimate of the response of path S(z), response $SE_{COPY}(z)$, and minimizing the difference between the resultant signal and error microphone signal err, adaptive filter 32 may adapt to the desired response of P(z)/S(z). In addition to error microphone signal err, the signal compared to the output of filter 34B by W coefficient control block 31 may include an inverted amount of downlink audio signal ds and/or internal audio signal ia that has been processed by filter response SE(z), of which response $SE_{COPY}(z)$ is a copy. By injecting an inverted amount of downlink audio signal ds and/or internal audio signal ia, adaptive filter 32 may be prevented from adapting to the relatively large amount of downlink audio and/or internal audio signal present in error microphone signal err. However, by transforming that inverted copy of downlink audio signal ds and/or internal audio signal ia with the estimate of the response of path S(z), the downlink audio and/or internal audio that is removed from error microphone signal err should match the expected version of downlink audio signal ds and/or internal audio signal ia reproduced at error microphone signal err, because the electrical and acoustical path of S(z) is the path taken by downlink audio signal ds and/or internal audio signal ia to arrive at error microphone E. Filter 34B may not be an adaptive filter, per se, but may have an adjustable response that is tuned to match the response of adaptive filter 34A, so that the response of filter 34B tracks the adapting of adaptive filter 34A.

To implement the above, adaptive filter 34A may have coefficients controlled by SE coefficient control block 33, which may compare a source audio signal (e.g., downlink audio signal ds and/or internal audio signal ia) and a playback corrected error, wherein the playback corrected error is equal to error microphone signal err after removal of the source audio signal (as filtered by adaptive filter 34A to represent the expected playback audio delivered to error microphone E) by a combiner 36. SE coefficient control block 33 may correlate the actual source audio signal with the components of the source audio signal that are present in error microphone signal err. Adaptive filter 34A may thereby be adapted to generate a secondary estimate signal from the source audio signal, that when subtracted from error microphone signal err to generate the playback corrected error, includes the content of error microphone signal err that is not due to the source audio signal.

The modified playback corrected error may be communicated to W coefficient control block 31 and compared with the filtered reference microphone signal ref, wherein the modified playback corrected error is equal to the playback corrected error after removal (e.g., by combiner 38) of a scaled anti-noise signal generated by a biasing portion comprising gain element 46 and filter 34C. Filter 34C may not be an adaptive filter, per se, but may have an adjustable response that is tuned to match the response of adaptive filter 34A, so that the response of filter 34C tracks the adapting of adaptive filter 34A. Gain element 46 may apply a multiplicative scaling factor and filter 34C may apply the response $SE_{COPY}(z)$ (which is a copy of SE(z)) to the anti-noise signal generated by filter 32 in order to generate the scaled anti-noise signal. Accordingly, a gain G of ANC system 30 (where the gain G is the ratio of the anti-noise signal generated by a typical ANC system without gain element 46 and filter 34C to the anti-noise generated by filter 32 of ANC circuit 30 depicted in FIG. 3) may be varied by modifying the scaling factor of gain element 46, without other parts of ANC circuit 30 compensating and nullifying the change in gain G as it is varied. The relationship between the gain G of filter 32 and the scaling factor k of gain element 46 may be given by the equation:

$$G=1/(1-k)$$

In order to compensate for changes in a distance between error microphone reference point ERP and drum reference point DRP, ANC circuit 30 may vary the scaling factor, and therefore the gain G, based on an estimation or other indication of the distance between error microphone reference point ERP and drum reference point DRP. Such distance may be estimated in any suitable manner, for example by detecting a pressure of wireless telephone 10 against a listener's ear 5 as described in U.S. patent application Ser. No. 13/844,602 filed Mar. 15, 2013, entitled "Monitoring of Speaker Impedance to Detect Pressure Applied Between Mobile Device in Ear," and/or as described in U.S. patent application Ser. No. 13/310,380 filed Dec. 2, 2011, entitled "Ear-Coupling Detection and Adjustment of Adaptive Response in Noise-Cancelling in Personal Audio Devices," in which distance may be estimated and/or pressure may be determined by analyzing the response SE(z) of filter 34A due to the fact that in certain personal audio devices, the response SE(z) may vary in amplitude within certain frequencies (e.g., less than 1-2 kilohertz) based on the pressure between speaker SPKR and the listener's ear 5, and thus, by examining amplitude of SE(z) at such frequencies, a pressure and/or distance may be estimated.

This disclosure encompasses all changes, substitutions, variations, alterations, and modifications to the exemplary embodiments herein that a person having ordinary skill in the art would comprehend. Similarly, where appropriate, the appended claims encompass all changes, substitutions, variations, alterations, and modifications to the exemplary embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

All examples and conditional language recited herein are intended for pedagogical objects to aid the reader in understanding the invention and the concepts contributed by the inventor to furthering the art, and are construed as being without limitation to such specifically recited examples and conditions. Although embodiments of the present inventions have been described in detail, it should be understood that various changes, substitutions, and alterations could be made hereto without departing from the spirit and scope of the disclosure.

What is claimed is:

1. A personal audio device comprising:

a personal audio device housing;

a transducer coupled to the personal audio device housing for reproducing an audio signal including both a source audio signal for playback to a listener and an anti-noise signal for countering the effects of ambient audio sounds in an acoustic output of the transducer;

a reference microphone coupled to the personal audio device housing for providing a reference microphone signal indicative of the ambient audio sounds;

an error microphone coupled to the personal audio device housing in proximity to the transducer for providing an error microphone signal indicative of the acoustic output of the transducer and the ambient audio sounds at the transducer; and a processing circuit comprising:

an adaptive filter having a response that generates an anti-noise signal from the reference microphone signal;

a secondary path estimate filter configured to model an electro-acoustic path of the source audio signal and have a response that generates a secondary path estimate from the source audio signal;

a biasing portion that generates a scaled anti-noise signal by applying a scaling factor and the response of the secondary path estimate filter to the anti-noise signal; and a coefficient control block that shapes the response of the adaptive filter in conformity with the reference microphone signal and a modified playback corrected error signal by adapting the response of the adaptive filter to minimize the ambient audio sounds in the error microphone signal, wherein a playback corrected error signal is based on a difference between the error microphone signal and the secondary path estimate and the modified playback corrected error signal is based on a difference between the playback corrected error signal and the scaled anti-noise signal.

2. The personal audio device of claim 1, wherein the scaling factor has a value between 0 and 1.

3. The personal audio device of claim 1, wherein the scaling factor defines a gain, wherein the gain is the ratio of the anti-noise signal that would be generated by filter without the biasing portion to the anti-noise generated by filter with the biasing portion.

4. The personal audio device of claim 1, wherein the value of the scaling factor is a function of a distance between the personal audio device and a portion of the listener.

5. The personal audio device of claim 4, wherein the distance is an estimated distance between the transducer and the listener's eardrum.

6. The personal audio device of claim 4, wherein:

the secondary path estimate filter is an adaptive filter, and the processing circuit further implements a secondary coefficient control block that shapes the response of the secondary path estimate filter in conformity with the source audio signal and the playback corrected error signal by adapting the response of the secondary path estimate filter to minimize the playback corrected error signal; and the distance is determined based on the response of the secondary path estimate filter.

7. The personal audio device of claim 1, wherein the value of the scaling factor is a function of a pressure applied to the personal audio device by the listener.

8. The personal audio device of claim 7, wherein the pressure is a pressure applied between the personal audio device and the listener's ear.

9. The personal audio device of claim 7, wherein:

the secondary path estimate filter is adaptive, and the processing circuit further implements a secondary coefficient control block that shapes the response of the secondary path estimate filter in conformity with the source audio signal and the playback corrected error signal by adapting the response of the secondary path estimate filter to minimize the playback corrected error signal; and the pressure is determined based on the response of the secondary path estimate filter.

10. A method for canceling ambient audio sounds in the proximity of a transducer of a personal audio device, the method comprising:

receiving a reference microphone signal indicative of the ambient audio sounds;

receiving an error microphone signal indicative of the output of the transducer and the ambient audio sounds at the transducer; and generating a source audio signal for playback to a listener;

adaptively generating an anti-noise signal for countering effects of the ambient audio sounds at an acoustic output of the transducer by adapting a response of an adaptive filter that filters the reference microphone signal in conformity with the reference microphone signal and a modified playback corrected error signal to minimize the ambient audio sounds in the error microphone signal;

generating a secondary path estimate from the source audio signal by filtering the source audio signal with a secondary path estimate filter modeling an electro-acoustic path of the source audio signal;

generating a scaled anti-noise signal by applying a scaling factor and a response of the secondary path estimate filter to the anti-noise signal; and combining the anti-noise signal with a source audio signal to generate an audio signal provided to the transducer;

wherein a playback corrected error signal is based on a difference between the error microphone signal and the secondary path estimate and the modified playback corrected error signal is based on a difference between the playback corrected error signal and the scaled anti-noise signal.

11. The method of claim 10, wherein the scaling factor has a value between 0 and 1.

12. The method of claim 10, wherein the scaling factor defines a gain, wherein the gain is the ratio of the anti-noise signal that would be generated by filter without the biasing portion to the anti-noise generated by filter with the biasing portion.

13. The method of claim 10, wherein the value of the scaling factor is a function of a distance between the personal audio device and a portion of the listener.

14. The method of claim 13, wherein the distance is an estimated distance between the transducer and the listener's eardrum.

15. The method of claim 13, further comprising:

shaping the response of the secondary path estimate filter in conformity with the source audio signal and the playback corrected error signal by adapting the response of the secondary path estimate filter to minimize the playback corrected error signal; and determining the distance based on the response of the secondary path estimate filter.

16. The method of claim 10, wherein the value of the scaling factor is a function of a pressure applied to the personal audio device by the listener.

17. The method of claim 16, wherein the pressure is a pressure applied between the personal audio device and the listener's ear.

18. The method of claim 16, further comprising:

shaping the response of the secondary path estimate filter in conformity with the source audio signal and the playback corrected error signal by adapting the response of the secondary path estimate filter to minimize the playback corrected error signal; and determining the pressure based on the response of the secondary path estimate filter.

19. An integrated circuit for implementing at least a portion of a personal audio device, comprising:

an output for providing a signal to a transducer including both a source audio signal for playback to a listener and an anti-noise signal for countering the effect of ambient audio sounds in an acoustic output of the transducer;

a reference microphone input for receiving a reference microphone signal indicative of the ambient audio sounds;

an error microphone input for receiving an error microphone signal indicative of the output of the transducer and the ambient audio sounds at the transducer, and a processing circuit comprising:

an adaptive filter having a response that generates an anti-noise signal from the reference microphone signal;

a secondary path estimate filter configured to model an electro-acoustic path of the source audio signal and have a response that generates a secondary path estimate from the source audio signal;

a biasing portion that generates a scaled anti-noise signal by applying a scaling factor and the response of the secondary path estimate filter to the anti-noise signal; and a coefficient control block that shapes the response of the adaptive filter in conformity with the reference microphone signal and a modified playback corrected error signal by adapting the response of the adaptive filter to minimize the ambient audio sounds in the error microphone signal, wherein a playback corrected error signal is based on a difference between the error microphone signal and the secondary path estimate and the modified playback corrected error signal is based on a difference between the playback corrected error signal and the scaled anti-noise signal.

20. The integrated circuit of claim 19, wherein the scaling factor has a value between 0 and 1.

21. The integrated circuit of claim 19, wherein the scaling factor defines a gain, wherein the gain is the ratio of the anti-noise signal that would be generated by filter without the biasing portion to the anti-noise generated by filter with the biasing portion.

22. The integrated circuit of claim 19, wherein the scaling factor is a function of a distance between the personal audio device and a portion of the listener.

23. The integrated circuit of claim 22, wherein the distance is an estimated distance between the transducer and the listener's eardrum.

24. The integrated circuit of claim 22, wherein:

the secondary path estimate filter is an adaptive filter, and the processing circuit further implements a secondary coefficient control block that shapes the response of the secondary path estimate filter in conformity with the source audio signal and the playback corrected error signal by adapting the response of the secondary path estimate filter to minimize the playback corrected error signal; and the distance is determined based on the response of the secondary path estimate filter.

25. The integrated circuit of claim 19, wherein the scaling factor is a function of a pressure applied to the personal audio device by the listener.

26. The integrated circuit of claim 25, wherein the pressure is a pressure applied between the personal audio device and the listener's ear.

27. The integrated circuit of claim 25, wherein:

the secondary path estimate filter is adaptive, and the processing circuit further implements a secondary coefficient control block that shapes the response of the secondary path estimate filter in conformity with the source audio signal and the playback corrected error signal by adapting the response of the secondary path estimate filter to minimize the playback corrected error signal; and the pressure is determined based on the response of the secondary path estimate filter.

* * * * *